United States Patent [19]

Lamadrid

[11] 4,397,642

[45] Aug. 9, 1983

[54] MOTOR DRIVEN OCCLUSION CONTROLLER FOR LIQUID INFUSION AND THE LIKE

[75] Inventor: Rene Lamadrid, Lake Forest, Ill.

[73] Assignee: Baxter Travenol Laboratories, Inc., Deerfield, Ill.

[21] Appl. No.: 336,154

[22] Filed: Dec. 31, 1981

[51] Int. Cl.³ .............................................. A61M 5/00
[52] U.S. Cl. ........................... 604/245; 128/DIG. 13; 137/486; 222/14; 222/52; 251/6; 251/9; 251/138; 251/249.5; 604/65
[58] Field of Search ............... 128/DIG. 12, DIG. 13; 137/486, 487.5; 222/14, 52, 59, 63; 251/6, 7, 9, 68, 138, 230, 249.5; 417/44; 604/34, 50–52, 153, 245–246, 250, 253

[56] References Cited

U.S. PATENT DOCUMENTS

| | | | |
|---|---|---|---|
| 3,197,068 | 8/1965 | Corbin et al. | 222/59 |
| 3,601,124 | 8/1971 | Petree | 222/63 |
| 4,105,028 | 8/1978 | Sadlier et al. | 222/59 |
| 4,261,388 | 4/1981 | Shelton | 137/486 |
| 4,278,085 | 7/1981 | Shim | 128/DIG. 12 |
| 4,355,638 | 10/1982 | Iwatschenko et al. | 128/DIG. 12 |

Primary Examiner—Richard J. Apley
Assistant Examiner—George Yanulis
Attorney, Agent, or Firm—Robert a. Benziger; John T. Winburn; Paul C. Flattery

[57] ABSTRACT

A parenteral solution administration system having a conduit for communication with a source of parenteral solution, a drip chamber carried by the conduit, drop detector circuit for detecting drops falling through the drip chamber and flow control circuit including an occlusion device moving between first and second positions for opening and closing the conduit. Feedback circuit is provided for controlling the flow control circuit to cause the rate of drops falling through the drip chamber, as sensed by the drop detector circuit, to correspond to a predetermined drop rate. The occlusion device is preferably operated by a stepper motor, and the system is disengagable so that at the occurrence of a predetermined circumstance, the occlusion device can be disengaged from the motor circuit and can be moved without corresponding action of the motor circuit.

16 Claims, 5 Drawing Figures

MOTOR DRIVEN OCCLUSION CONTROLLER FOR LIQUID INFUSION AND THE LIKE

TECHNICAL FIELD

This application relates to an improvement in the precise delivery of typically small quantities of liquid through tubing. The invention is contemplated specifically for use in the administration of parenteral solutions to patients in hospitals and the like, but it also may be used for simplified metering of any liquid in precise quantities over a desired period of time into chemical or biological reactors, industrial processes, and the like.

While the administration of parenteral solutions is a common practice in hospitals, and great quantities of equipment of many different types are sold for the purpose of providing such administration, in many instances the medical situation calls for the administration of precisely controlled amounts of medication on a continuous drip basis over a period which may last several days or weeks. Cancer chemotherapy agents, for example, may be administered in this manner.

For these agents, and for many other medications, they must, of course, be administered to the patient in sufficient quantities to be effective, and often a uniform, continuous low volume dose is required. At the same time, an accidental increase in the flow rate can be life threatening in the case of some medications, and thus totally must be avoided.

Conventional, gravity-operated parenteral solution equipment is sometimes subject to unplanned increases in the flow rate due to cold flow of the plastic tubing in the area where the flow control clamp presses it, and thus may be unsuitable for the administration of certain critical dose medication. It also is not able to compensate for any flow rate increases which may be induced by other factors.

DESCRIPTION OF PRIOR ART

In the prior art, numerous patents exist which suggest various systems for controlling the flow of parenteral solution through a large assortment of electronic devices which purportedly provide improved flow accuracy. As a typical example of such prior art, drops of the solution are formed and fall through a conventional drip chamber in an administration set and are detected as they fall by a drop detector which may operate on photometric principles, by sensing variations in capacitance, or the like. A flow control clamp valve or other occlusion device is provided in the flow conduit and is controlled by a typically electronic feedback means for sensing the drop rate in the drip chamber and appropriately controlling the valve so that the drop rate falls within desired parameters.

Systems of this type can exhibit a significant disadvantage in the instance of a power failure. In such an instance, the flow control clamp valve or other occlusion device remains fixed in its last setting, so that liquid keeps on flowing at whatever the setting of the device was at the last moment. This setting may be excessive over the long run, since the clamp or valve setting of an average flow control system tends to oscillate between more open and less open positions on a moment-by-moment basis to obtain the overall desired flow rate. If a power failure occurs while the clamp or valve is at a momentarily relatively open position, the patient may receive a critical overdose of medicament before the nurse has a chance to correct the situation.

As another disadvantage, in many items in the prior art, a pump is used to propel the solution through the set. This carries its own hierarchy of risks, and requires the presence of safety systems to prevent the pumping of air into the patient in the event that the source of parenteral solution runs dry. Such safety systems are, of course, subject to breakdown and failure, and the consequences of that also potentially are fatal.

In accordance with this invention, a system is disclosed which can provide precisely measured amounts of parenteral solution to a patient through a system which is preferably gravity operated, for advantages of safety and simplicity. The system of this invention is also fail safe so in the event of a power failure the system can shut off. Also, it exhibits improvements of reliability of operation and cost effectiveness.

DISCLOSURE OF INVENTION

In this invention a solution administration system is provided which comprises a conduit proportioned for connection with a source of parenteral solution at one end for conveying the solution from the source to a patient. A drip chamber is carried by the conduit, and drop detector means are provided for detecting drops falling through the drip chamber.

Flow control means are also provided, including an occlusion device movable between a first position for compressing the conduit to occlude flow therethrough, and a second position to permit flow through the conduit. Feedback means are provided for controlling the flow control means, to cause the rate of drops falling through the drip chamber as sensed by the drop detector means to correspond to a predetermined drop rate.

In accordance with this invention, the feedback means comprises a rotatable ring carrying teeth on at least one periphery thereof. Gear means are rotatable about the teeth on that one periphery, to rotate an arm member carried by the gear means. The arm member is connected to the occlusion device to move the occlusion device between open and closed positions as the gear means is rotated between the first and second rotating positions.

Logic means are provided, along with motor means controlled by the logic means. The logic means is responsive to the drop detector means to cause the motor means to rotate the gear means between the first and second positions, to control the rate of drops falling through the drip chamber.

Retaining means are provided to normally prevent rotation of the ring. Means are also provided for disengaging the retaining means from its retention of the ring at the occurrence of a predetermined circumstance so that the occlusion device becomes disengaged from the motor means and can be moved without corresponding action of the motor means, so long as the ring is freely rotatable. The system may then be reconnected by actuation of the retaining means, to again prevent rotation of the ring.

While the invention of this application is described in conjunction with a solution administration system, it is also contemplated that it may be used in other valving systems as may be desired, wherever precise control of an occlusion device or simply a movable arm controlled by preferably a stepping motor is desired, in which the operative connection between the motor and the arm can be eliminated by permitting the ring described above to rotate.

Typically the rotatable ring carries teeth on the inner and outer peripheries thereof, with the gear means being rotatable about one of the peripheries of the ring, typically the inner periphery. The retaining means then may project between the teeth of the other of the peripheries of the ring to normally prevent rotation of the ring, and may be withdrawn upon the occurrence of the predetermined circumstance. For example, the retaining means may be driven into its ring-retaining relation by the action of a solenoid. In the event of a power failure, a spring causes the retaining means to be withdrawn from its retaining relation with the ring, permitting the ring to freely rotate, since the solenoid will have ceased its normal operation of urging the retaining means into engagement with the ring.

Typically the occlusion device is connected to a spring which biases it toward the closed position. Accordingly, the occlusion device spontaneously closes when the retaining means is deactivated, for example by being withdrawn from between the teeth of one of the peripheries of the ring to permit free rotation of the ring. Thus, in the event of a power failure the system can shut off in a fail-safe manner.

The gear means may comprise a plurality of planetary gears carried by a platform member which, in turn, carries the arm member described above. A central "sun" gear is provided, engaging the planetary gears, and a shaft may extend from the central gear to be rotated by the motor means.

The arm member may comprise a plurality of pivotally joined links positioned to rotate the occlusion device which may be also pivotally mounted.

DESCRIPTION OF DRAWINGS

Referring to the drawings.

DESCRIPTION OF SPECIFIC EMBODIMENT

Figure 1:
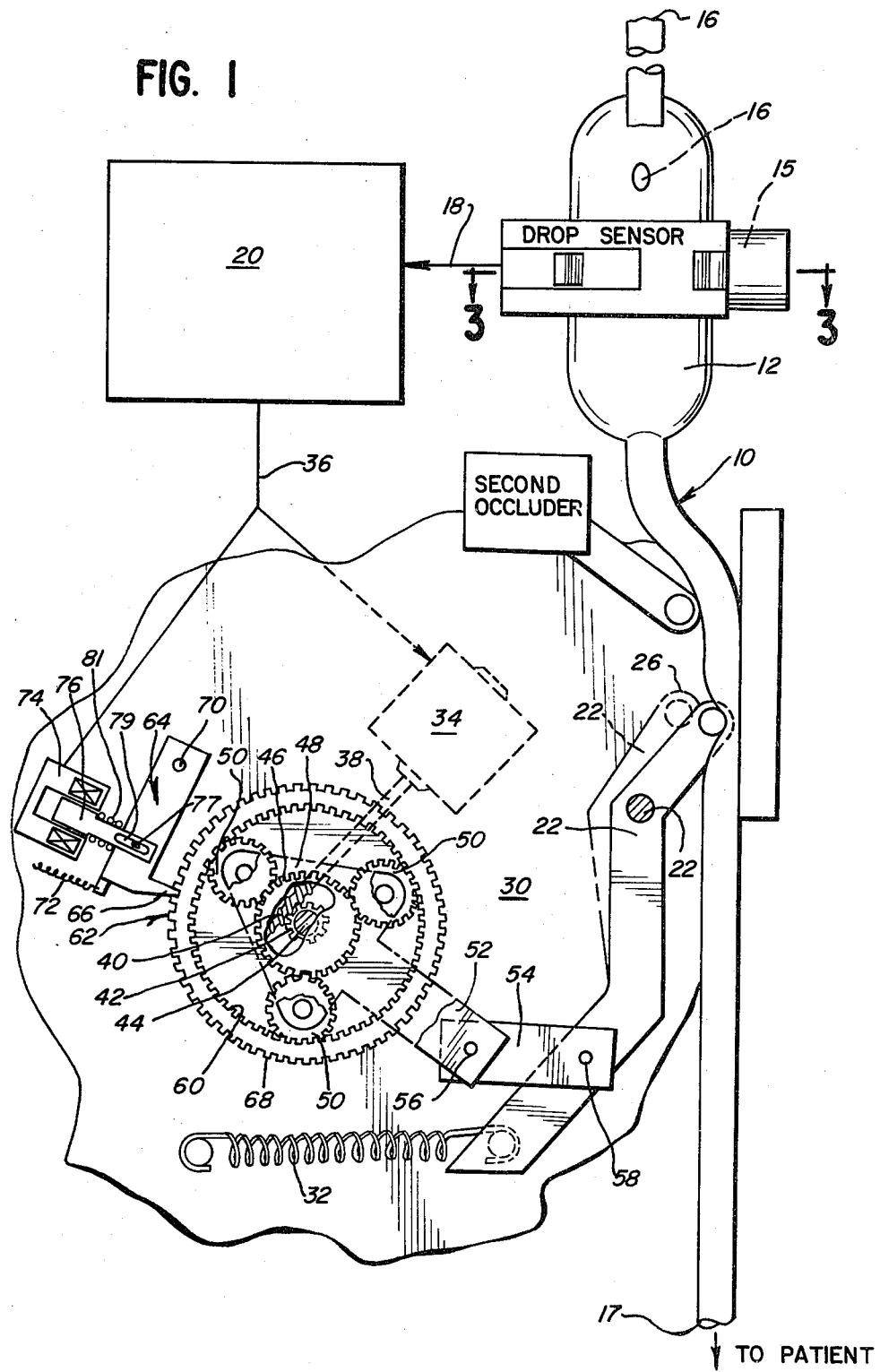
FIG. 1 is a partially schematic view of the apparatus of this invention.
Figure 2:
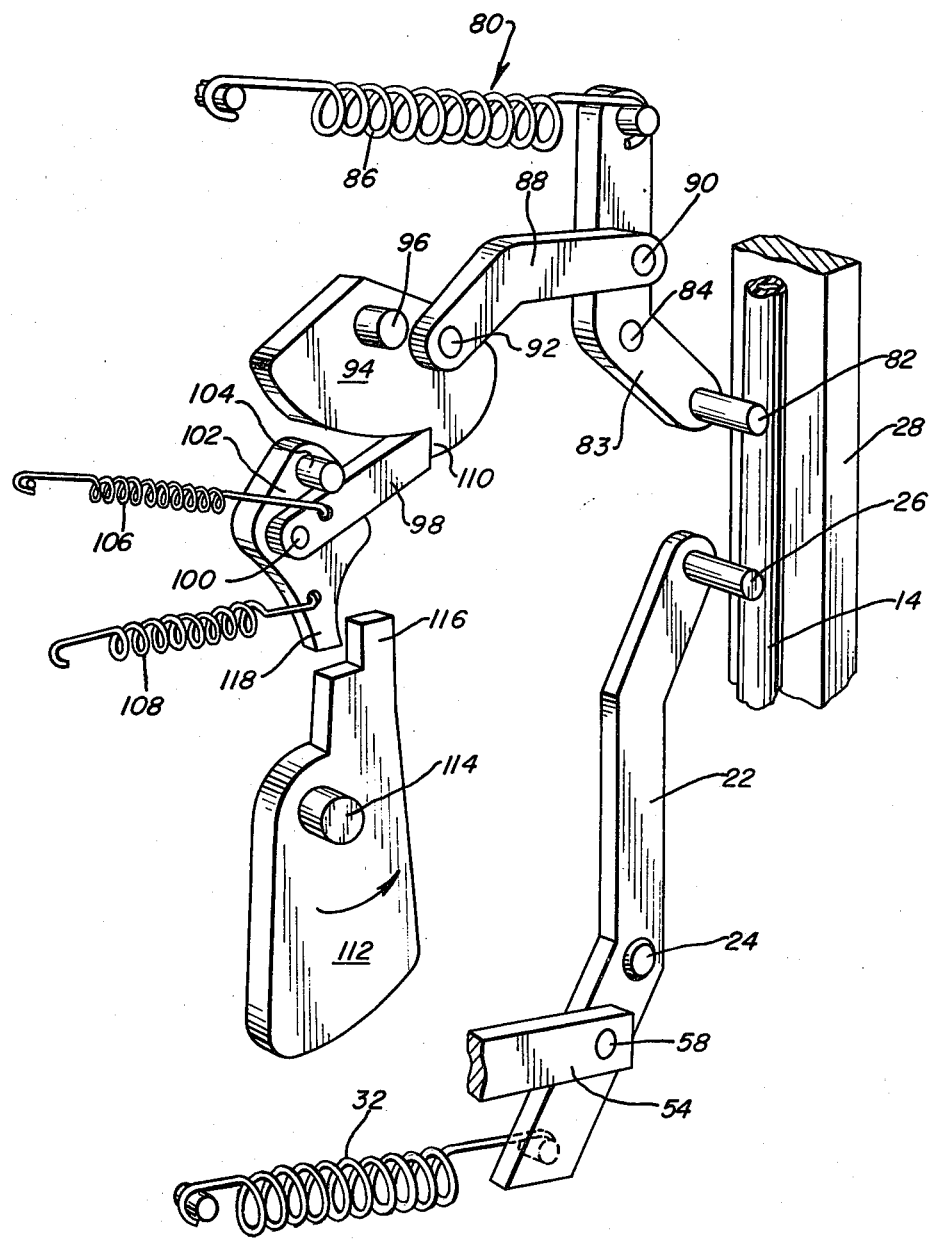
FIG. 2 is a fragmentary perspective view, with parts removed, of a portion of the apparatus of this invention, particularly the occlusion system.

Referring to FIGS. 1 and 2, a conventional plastic parenteral solution set 10 may be provided, having flexible, collapsible tubing 14 and a drip chamber 12 of conventional design. Tubing 14 may have an upper end 16 which is conventionally adapted for connection with a source of parenteral solution, while its lower end 17 may carry a luer connection for receiving an intravenous needle for entry into the patient's venous system. Alternatively, tubing 14 may be adapted for communication with a Y site in an added parenteral solution set which, in turn, can communicate with the patient in accordance with the disclosure of U.S. Pat. No. 4,105,029, for example. Thus while the upper end 16 of tubing 14 communicates with a source of critical medication, the added set to which it connects may connect to a source of normal saline solution, which is administered to the patient at a rate to keep the vein open in the event that the flow through tubing 14 is terminated or interrupted.

A drop detector 15 is provided adjacent drip chamber 12 to detect drops 19 as they pass through the chamber. Drop detector 15 may be of any of numerous disclosed designs for drop detectors, and may be of an optical detector type, although other types of drop detectors may be utilized as well, for example, a drop detector utilizing capacitance principles.

When drop detector 15 detects a drop, a signal is sent through line 18 to feedback and control circuit 20, which may also be of conventional design. The rate of signals received from drop detector 15 is timed, and compared with a reference standard rate in circuitry 20, to determine whether the drop rate as detected is greater, less than, or equal to the desired reference drop rate, which may be set by the user.

Flow control means is provided as an occlusion system, including a clamp valve member 22 which is a bar pivotally mounted about pivot 24 and carrying pressure member 26, positioned to compress tube 14 against plate 28 to a variable degree dependent upon the rotational position of clamp member 22. Pressure members 26, 28 may alternatively be metal rods between which tubing 14 extends.

Clamp member 22 can move about pivot 24 between a first rotational position shown in full lines for compressing tubing 14 to block flow therethrough, and a second rotational position, shown partially in phantom lines, to permit flow through tubing 14.

Clamp member 22 is secured to a portion of frame 30 of the system by pivot 24, and also spring 32, with spring 32 being provided to bias clamp member 22 into its first, flow blocking position in which tubing 14 is pinched shut at the area between members 26 and 28.

Feedback means are provided to control the position of clamp member 22 in a manner responsive to the drop rate detected in drop detector 15.

The feedback means includes the control circuit 20 described above, which controls the operation of stepper motor 34 through line 36. Stepper motor 34 operates shaft 38, which terminates in gear 40, which may be a worm gear as shown, a spur gear, or the like. Gear 40 in turn communicates with gear 42, which is carried on shaft 44, which shaft also carries "sun" gear 46. Shaft 44 is carried by platform member 48, which is a plate of any desired shape, particularly shown to be generally triangular in the specific embodiment shown, with rotatable planetary gears 50 carried on platform member 48 at each corner and engaging "sun" gear 46. Platform member 48 also rigidly carries a first arm member 52, which is pivotally joined to second arm member 54 at pivot 56. Second arm member 54 is pivotally joined to clamp member 22 at pivot 58, so that as platform member 48 rotates, the rotary motion is transmitted through arm members 52, 54 into pivotal motion of clamp member 22, permitting clamp member 22 to rotate between its first and second positions for control of flow through tubing 14.

The relative length and angular relationship of first and second arm members 52, 54 may vary as desired. For example, the arm members 52, 54 may occupy approximately a 90° angle to each other as an alternative to the specific relationship shown.

Planetary gears 50 are also in engaging relationship with a gear track on the inner periphery 60 of ring 62, which is carried on and rotatable about planetary gears 50. However, ring 62 is normally held in nonrotating position by the action of retaining member 64, which carries a retaining finger 66 that is proportioned to fit between the gear teeth of outer periphery 68 of ring 62 as shown.

Retaining member 64 is mounted on pivot 70 so that it can rotate, being urged by spring 72 to rotate out of its engaging relation with the gear teeth of outer periphery 68, which consequently permits the free rotation of ring 62. However, solenoid 74 is positioned in operative relation with core 76 of retaining member 64 in such a manner that when solenoid 74 is actuated, retaining member 64 is pivoted in counterclockwise relation so that retaining finger 66 fits in between two of the gear teeth of outer periphery 68 of ring 62. Thus, as long as solenoid 74 is actuated, ring 62 cannot rotate.

Core 76 is pivotally mounted on retaining member 64 at pivot 77 which fits in slot 79 of core 76. Spring 81 permits a small amount of axial motion of core 76 relative to retaining member 64 so that solenoid 74 can actuate even if retaining finger 66 rests directly on a gear tooth of the outer periphery 68 of ring 62. Finger 66 is biased to drive in between one of said gear teeth as soon as ring 62 is rotated to any significant extent for retention of the ring from then on until solenoid 74 is deactivated.

Alternatively, the retaining system for ring 62 could be a simple brake band system with a solenoid for causing it to grip or release ring 62 about its outer periphery, for equivalent results to that which is described above.

The retaining means 64 and related parts may be provided through a clutch system sold by the Hurst Manufacturing Corp. of Princeton, Indiana. In that particular system, energizing the solenoid pulls a solenoid armature toward the solenoid, causing a pawl functionally similar to member 64 to engage ring 62. Springs cause disengagement of the pawl upon deactivation of the solenoid.

A second occluder member 80 may be provided for safe operation of the device of this invention by preventing uncontrolled flow through tubing 14 in the event the door or a hatch of the device is opened for access which may have the effect of causing pressure member 26 to disengage from tubing 10. In the event of the opening of a door or hinge, pressure member 82, carried on movable arm 83, can move to close flow through tubing 14 causing the device to have a positive clamping off of tubing 14 in the event that the door or hatch is opened.

As shown in FIG. 2, operating arm 83 carrying occlusion member 82 is mounted to the housing or frame member, not shown, in pivotal relation about pivot 84, being biased by tension spring 86 to move in counterclockwise manner to occlude flow through tubing 14. Pivotally mounted arm 88 is mounted to operating arm 83 at a pivot 90 above pivot 84 at one end. Arm 88 is pivotally mounted at pivot 92 at its other end to rotationally mounted operating member 94. Member 94 is also pivotally mounted to the housing or frame member about pivot 92. Latching arm 98 is pivotally mounted at pivot 100 to rotatable member 102 which is pivotally mounted to the housing or frame member at pivot 100. Arm 98 is biased as shown by tension spring 106 against post 104, while member 102 is biased to rotate in a counterclockwise manner by tension spring 108. Arm member 98 projects at its outer end into notch 110 defined by member 94, which is mounted on pivot 96.

Figure 5:
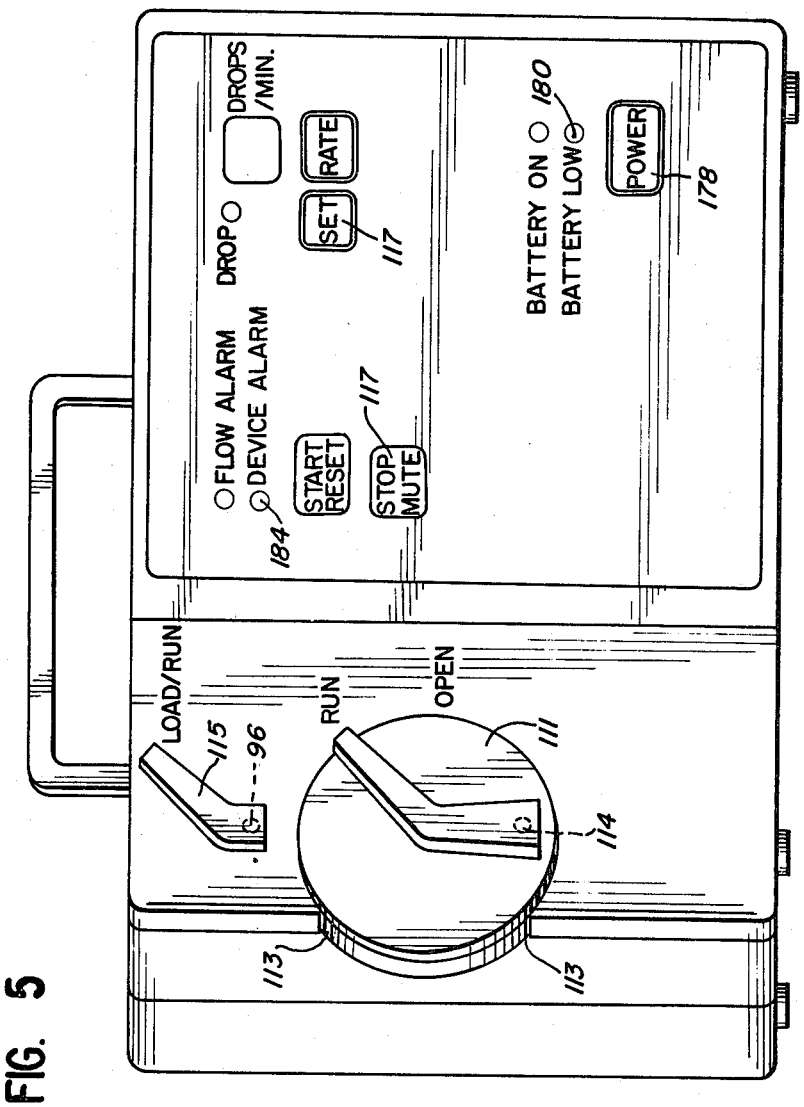
FIG. 5 is a perspective view of the front panel of the apparatus of this invention.

Rotatable cam member 112 may be operated by the opening or closing rotatable access door 111 (FIG. 5) of the device to rotate with door 111 about pivot 114 so that finger member 116 impinges against lower knuckle 118 of plate 102 as access door 111 is opened.

Plate 102 is thus forced to move clockwise as finger member 116 passes in rotary motion in counterclockwise manner in a direction to displace lower knuckle 118, moving latching arm 98 out from engagement with notch 110. This permits spring 86 to cause operating member 94 to pivot in clockwise manner, as arm 88 moves to the left, and arm 83, carrying occlusion member 82, is moved into closed position.

Thus the opening of access door 111 causes the apparatus to shut down, preventing flow from passing through tubing 14.

As access door 111 is further opened, finger member 116 continues to move in counterclockwise manner out of engagement with knuckle 118, so that plate 102 rotates back to its original position, urged by spring 106. However, operating member 94 remains in a clockwise advanced rotational position with respect to its position shown in FIG. 2 so that arm 98 cannot engage notch 110, but is biased by spring 106 against operating member 94.

When access door 111 is opened, tubing 14 and the respective clamping members or occluders 82, 26 are exposed. Tubing 14 can enter and exit through slots 113. Arms 83 and 22 can be manually lifted to remove the tubing and to install fresh tubing as may be desired.

When occluder 82 is lifted, a reverse motion from that described above takes place, in that arm 83 rotates clockwise, and arm 88 is retracted to the right. Operating member 94 also rotates counterclockwise in that instance.

Also, when door 111 is opened, solenoid 74 may be deactivated, causing retaining finger 66 to be withdrawn from retaining relation with the gears of outer periphery 68 of ring 62. Thus when door 111 is opened, arm 22 and occluder 26 may be freely retracted by the fingers against the biasing pressure of spring 32 for removal of replacement of tubing 14. However, when door 111 is closed again and when solenoid 74 is reactivated, arm 22 and occluder 26 become locked again into the position dictated by the control apparatus.

With a newly installed tubing 14, one can close door 111, which causes cam member 112 to rotate in clockwise manner, with finger member 116 passing once again into engagement with lower knuckle 118, causing plate 102 to move counterclockwise. However, it can be seen from FIG. 2 that the counterclockwise motion of plate 102 does not effect the position of arm 98, since plate 102 can rotate counterclockwise to a certain degree without any corresponding motion of arm 98.

After finger 116 has passed a sufficient clockwise distance to be out of engagement once again with knuckle 118, rotatable member 102 snaps back into its position as shown in FIG. 2 impelled by spring 108, and door 111 is closed.

The device may then be "cocked" by manipulating lever 115 on the front panel, carried by pivot shaft 96, to rotate operating member 94 counterclockwise to permit arm 98 to snap into engagement with notch 110 again so that occluder 82 does not close tubing 14. Thereafter, whenever door 111 is opened, the process previously described causes latching arm 98 to be again pushed out of engagement by member 104 of rotatable member 102, to cause occluder 82 to snap into occluding relation with tube 14. Thus the apparatus of this invention spontaneously and immediately shuts off when door 111 is opened, but it is easily recocked by lever 115 for easy installation of a new tube 14. This provides safe but convenient operation of the apparatus.

The front panel of the apparatus may also contain various indicators 117 as may be desired, to indicate drop flow rate, the condition of the battery, alarms as desired, and the like.

Figure 3:
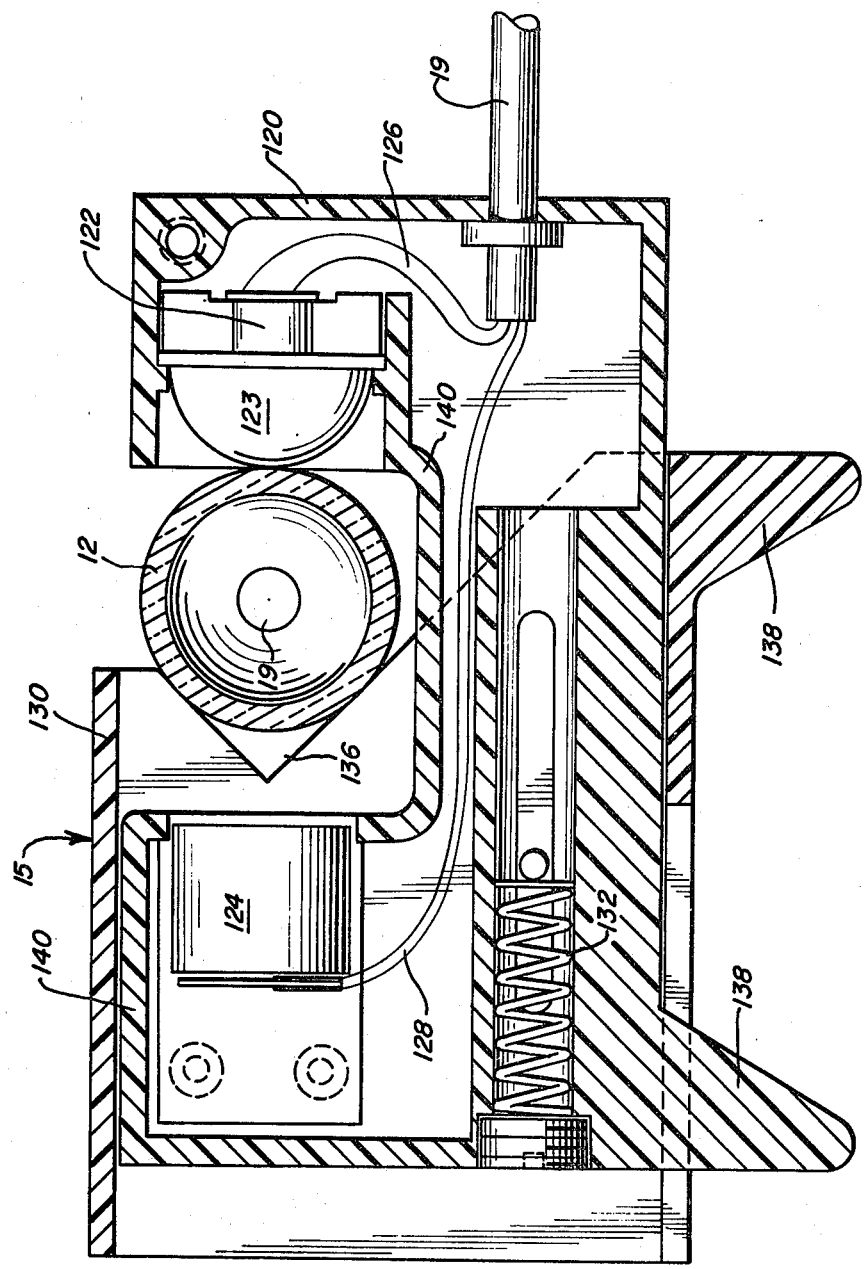
FIG. 3 is a longitudinal sectional view of the drop sensor of this invention.

A specific design for drop detector 15 is disclosed in FIG. 3. The drop detector 15 has a housing 120 which carries a light 122 such as a light which is adapted for example by lens 123 to project a beam of light into a light receptor 124, typically a "photovoltaic diode" or the like. Leads 126, 128 are provided to provide power for the light source 122 and to communicate signals from the receptor 124 indicative of whether light is sensed or whether a change in the light pattern is sensed of the type that might be provided by a drop 19 falling through drip chamber 12. Such an event impinges the beam of light from source 122 to receptor 124 changing the characteristics of light sensed by receptor 124 and causing a corresponding signal to appear on line 128 and to be applied to the electronic circuitry shown in FIG. 4.

Detector 15 is retained about drip chamber 12 by a spring biased housing member 130 which is biased by spring 132 toward a closed position so as to gently press against drip chamber 12. V-shaped cuttings 136 in the side walls of sliding housing 130 retain the drip chamber 12 in the desired position in respect of light source 122. Ears or projections 138 are provided to permit one to open sliding housing 130 to insert drip chamber 12 with spring member 132 then biasing sliding housing 130 back toward a closed position to cause drip chamber 12 to be firmly retained in the proper position. Light source 122 and receptor 124 are mounted on inner housing 140, thus being permanently positioned with respect to each other by a predetermined and fixed spacing and alignment so that the two members do not need to be realigned between uses or otherwise calibrated in a manner that might be necessary if they were movable with respect to each other.

Thus the drop detector 15 is capable of receiving drip chambers of different sizes and can be used to detect drops in any of a variety of fluid flow sets.

Figure 4:
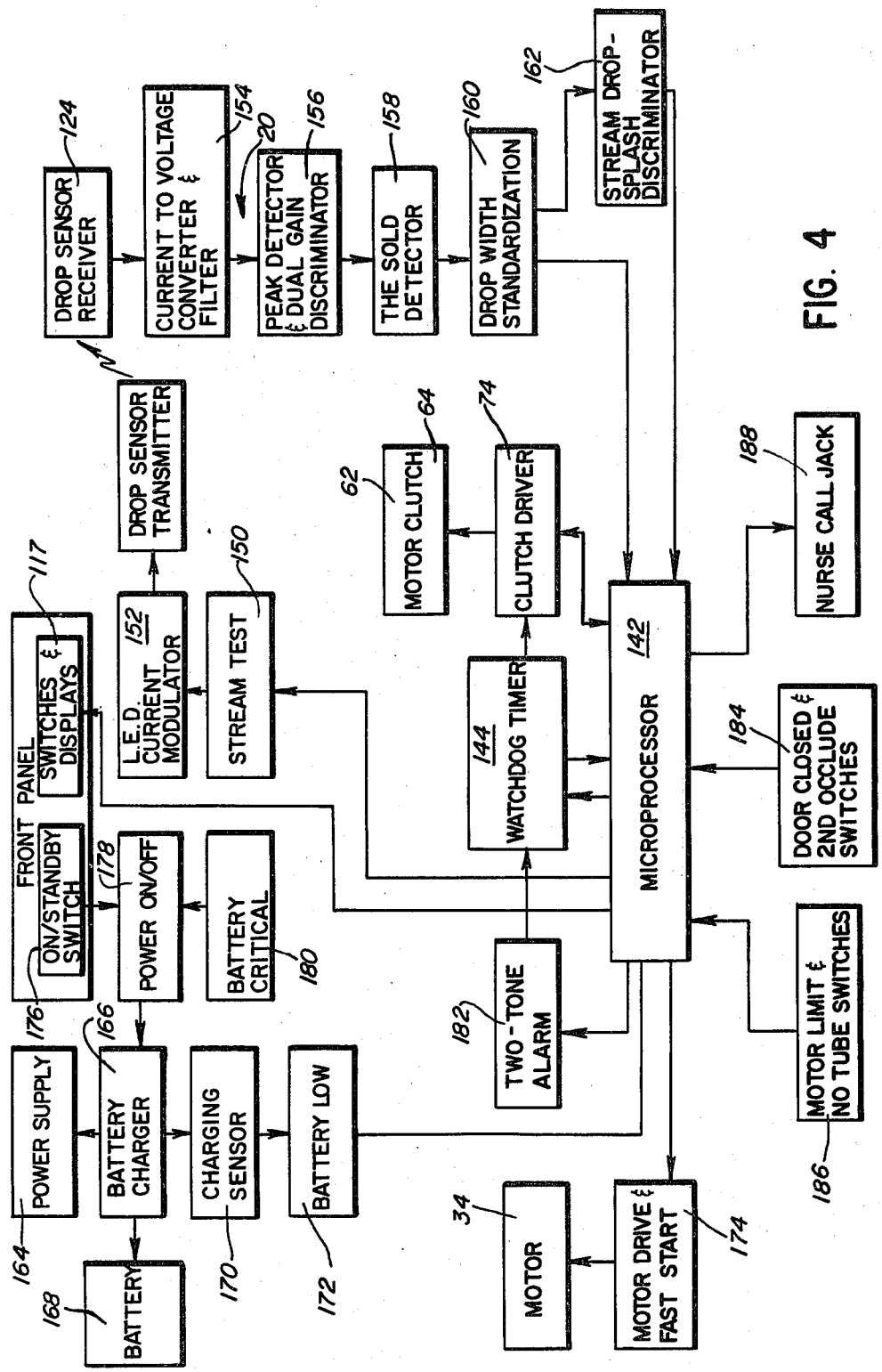
FIG. 4 is a block diagram of the electronic system used with this invention.

Referring to FIG. 4, a block diagram of the electronics and various functions of a representative control circuit 20 for use with this invention are disclosed. A microprocessor 142 governs the various functions of the circuitry 20. By way of example, one such microprocessor is an Intel 8039 microprocessor. Microprocessor 142 communicates with a watchdog timer 144 which causes the microprocessor to evaluate the flow situation periodically (typically measured in fractions of a second) for continuous monitoring of the flow rate. Watchdog timer 144 and microprocessor 142 communicate with clutch driver 74, which in this example corresponds to solenoid 74 in FIG. 1. Clutch driver 74 governs motor clutch 62, 64, which in this example corresponds to pawl 64 and toothed ring gear 62, in the manner previously described for control and rapid release of pressure member 26.

Stream test circuit 150 communicates with LED current modulator 152 which in turn activates the LED or drop sensor transmitter light source 122 to provide a beam of light which is pointed at the sensor 124. Sensor 124 receives the beam of light as modulated by drops 19 falling through the beam sending a signal through line 128 within cable 18 back to circuitry 20. Control circuitry 20 further includes a current to voltage converter and filter 154, a peak detector and dual gain discriminator 156, a threshold connect detector 158 and a drop width standardization circuit 160 which communicates again with microprocessor 142. A stream drop/discriminator 162 also receives signals from circuit 160 and communicates with microprocessor 142.

Power supply 164 is provided in communication with a battery charger 166, electrically connected to a battery 168 which is provided for emergency power in the event of power failure, through battery maintenance circuitry such as charging sensor 170 and battery low indicator 172 to microprocessor 142 from which the entire system may be energized. Motor 34 receives its power through motor drive and fast start system 174 which is controlled electrically by microprocessor 142.

Other illustrated features include front panel switches 156 as indicated, including a power on or off switch 178 and a battery critical indicator 180 and a desired fluid delivery rate setable as an input to the microprocessor 142.

An alarm system may be provided communicating with microprocessor 142 and watchdog timer 144 to indicate a malfunctioning period. Switches 184 may be provided to indicate by visual display closing of the door or hatch to actuate pressure member 26 and deactivate pressure member 82. Motor limit and no tube switches 186 are provided, as is a nurse call jack 188.

Accordingly, the operation of the apparatus proceeds as follows:

Drop detector 15 detects drops 19 falling through drip chamber 12. Signals corresponding to the individual drops 19 are sent through line 18 to circuitry 20, where the drop rate is compared electronically with the predetermined desired rate, which typically may be set into the circuitry by the user by manipulation of conventional controls. A resulting signal is sent through line 36 to stepper motor 34 in the event that the perceived drop rate is not optimum, causing stepper motor 34 to rotate shaft 38 either clockwise or counterclockwise to increase or decrease the drop rate. This, in turn, through gears 42 and 46, causes platform member 48 to rotate along with planetary gears 50. Accordingly, arms 52, 54 cause clamp member 22 to either open or close the orifice defined between clamping bars 26, 28 in tubing 14. Thus, precise, moment-by-moment, automatic control can be provided to the flow rate for extreme accuracy of administration through tubing 14.

Through all this operation, solenoid 74 is actuated, holding retaining finger 66 into retaining relation with the gears of outer periphery 68 of ring 62, solenoid 74 being connected to the on-off switch of the system, so that it is constantly activated while the system is on.

In the event of a power or battery failure, solenoid 74 is deactivated. Spring 72 then rotates retaining member 64 and finger 66 out of engagement with ring 62. This permits spring 32 to close clamp member 22 completely, so that flow through tubing 14 terminates, arm members 52, 54 being freely rotatable because ring 62 is freely rotatable. This permits the planetary gears 50 to rotate with freely rotating ring 62 about sun gear 46, even though the sun gear remains linked to the stepper motor 34 and thus is nonrotatable when motor 34 is not operated.

On reactivation of the apparatus, solenoid 74 advances retainer member 64 so that finger 66 advances in between two gear teeth of outer periphery 68 (which may be outwardly tapered if desired to facilitate that advancement) to retain ring 60 in nonrotatable position for operation of the apparatus. It can be seen that the apparatus will operate in any rotational position of ring 62 and that ring 62 can rotate to permit the closing of clamp valve 22 upon shut off of the apparatus.

In the event that finger 66 is driven by solenoid directly against the tooth of the outer periphery 68 and thus fails to move in between a pair of teeth, when stepper motor 34 begins to operate to rotate platform 48, ring 62 will tend to rotate with it to a slight degree, permitting finger 66 to be driven in between a pair of the teeth of periphery 60.

Optional second occluder 80 operates in conjunction with the above in the manner previously described.

The above has been offered for illustrative purposes only, and is not intended to limit the scope of the invention of this application, which is as set forth in the claims below.

That which is claimed is:

1. In a solution administration system comprising a conduit proportioned for connection with a source of parenteral solution at one end for conveying said solution from said source to a patient, a drip chamber carried by said conduit, drop detector means for detecting drops falling through said drip chamber, flow control means including an occlusion device movable between a first position for compressing said conduit to occlude flow therethrough and a second position to permit flow through said conduit, and feedback means for controlling said flow control means to cause the rate of drops falling through the drip chamber as sensed by the drop detector means to correspond to a predetermined drop rate, wherein the improvement comprising, in combination:

said feedback means comprising a rotatable ring carrying teeth on at least one of its inner and outer peripheries, gear means rotatable in cooperation with the teeth of said periphery to rotate an arm member carried by said gear means, said arm member being connected to said occlusion device to move said occlusion device between open and closed positions as said gear means is rotated;

logic means, motor means controlled by the logic means and drivingly engaging said gear means; said logic means being responsive to said drop detector means to cause the motor means to rotate said gear means to control the rate of drops falling through the drip chamber;

retaining means normally preventing rotation of said ring; and means for deactivating said retaining means at the occurrence of a predetermined circumstance, whereby said occlusion device is disengaged from the motor means and can be moved without corresponding action of the motor means.

2. The system of claim 1 in which said occlusion device is connected to a spring which biases it to the closed position, whereby said occlusion device spontaneously closes when the retaining means is deactivated.

3. The system of claim 1 in which said gear means is rotatable about teeth carried by the inner periphery of said ring.

4. The system of claim 3 in which said gear means comprises a plurality of planetary gears carried by a platform member, a central gear engaging said planetary gears, and a shaft extending from said central gear and rotatable by said motor means.

5. The system of claim 4 in which said shaft carries gear teeth, the drive shaft of said motor means terminating in a gear which engages said shaft.

6. The system of claim 1 in which said motor means is a stepping motor.

7. The system of claim 1 in which said retaining means defines a finger normally projecting between said teeth and held in said normally projecting position by an activated solenoid, and spring means for withdrawing said finger from between the teeth when the solenoid is deactivated.

8. The system of claim 1 in which said arm member comprises a plurality of pivotally joined links positioned to rotate said occlusion device.

9. The solution administration system of claim 1 in which said flow control means also includes a second occlusion device movable between a first position for compressing said conduit to occlude flow therethrough and a second position to permit flow through said conduit, said system including an openable and closeable access door for said flow control means, and means causing said second occlusion device to move to said first position on opening of said door.

10. The solution administration system of claim 9 in which means are provided to permit manual movement of said second occlusion device to the second position with the access door open, said occlusion device being biased toward the first position prior to and on closing of the access door.

11. In a solution administration system comprising a conduit proportioned for connection with a source of parenteral solution at one end for conveying said solution from said source to a patient, a drip chamber carried by said conduit, drop detector means for detecting drops falling through said drip chamber, flow control means including an occlusion device movable between a first position for compressing said conduit to occlude flow therethrough and a second position to permit flow through said conduit, and feedback means for controlling said flow control means to cause the rate of drops falling through the drip chamber as sensed by the drop detector means to correspond to a predetermined drop rate, the improvement comprising, in combination:

said feedback means comprising a rotatable ring carrying teeth on the inner and outer peripheries thereof;

gear means rotatable about one of the peripheries of said ring to rotate an arm member carried by said gear means, said arm member being operatively connected to said occlusion device to move said occlusion device between open and closed positions as said gear means is rotated between first and second rotating positions;

logic means; motor means controlled by the logic means and drivingly engaging said gear means; said logic means being responsive to said drop detector means to cause the motor means to rotate said gear means between said first and second positions, to control the rate of drops falling through the drip chamber;

retaining means normally projecting between teeth of the other of said peripheries of the ring to normally prevent rotation of said ring; and means for withdrawing said retaining means from between the teeth of the other of said peripheries at the occurrence of a predetermined circumstance, whereby said occlusion device is disengaged from the motor means and can be moved without corresponding action of the motor means.

12. The solution administration system of claim 11 in which said flow control means also includes a second occlusion device movable between a first position for compressing said conduit to occlude flow therethrough and a second position to permit flow through said conduit, said system including an openable and closeable access door for said flow control means, and means causing said second occlusion device to move to said first position on opening of said door.

13. In a solution administration system comprising a conduit proportioned for connection with a source of parenteral solution at one end for conveying solution from said source to a patient, flow control means for controlling the rate of flow through said conduit, said flow control means also including an occlusion device movable between a first position pressing said conduit to occlude flow therethrough and a second position to permit flow through said conduit, and an openable and closeable access door for the flow control means, the improvement comprising, in combination:
means causing said occlusion device to spontaneously move to said first position on opening of the door.

14. The solution administration system of claim 13 in which means are provided to permit manual movement of said occlusion device to the second position with the access door open, said occlusion device being biased toward the first position prior to and on closing of the access door.

15. The solution administration system of claim 13 including means for mmoving said occlusion device from the first to the second position and retaining it in the second position after closing of said door.

16. In a flow controller for use with a solution administration system of the type having a fluid conduit for communicating a source of parenteral solution to a patient wherein the fluid conduit includes a drip chamber, the flow controller having a drop sensor operatively engaging the drip chamber to sense the passage of drops therethrough, electronic circuit means for comparing the rate of sensed drops with a selectable rate and variable occlusion means including a conduit clamp member operable in response to the electronic circuit means variably to control the passage of fluid through the fluid conduit, improved variable occlusion means comprising in combination:
electric motor drive means; and
releasable gear train means operatively coupled to the electric motor drive means and in constant engagement with the clamp member; said releasable gear train means including a selectably releasable connection operable to permit relative motion between components of the gear train means upon the occurrence of a preselected condition.

* * * * *